US006658296B1

United States Patent
Wong et al.

(10) Patent No.: US 6,658,296 B1
(45) Date of Patent: Dec. 2, 2003

(54) IMPLANTABLE CARDIOVERTER DEFIBRILLATOR HAVING AN ARTICULATED FLEXIBLE CIRCUIT ELEMENT AND METHOD OF MANUFACTURING

(75) Inventors: Kenneth Wong, Saratoga, CA (US); Timothy A. Fayram, Gilroy, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 197 days.

(21) Appl. No.: 09/886,321

(22) Filed: Jun. 19, 2001

(51) Int. Cl.[7] .................. A61N 1/36; A61N 1/375; A61N 1/362
(52) U.S. Cl. ............................ 607/37; 607/9
(58) Field of Search .................. 607/4, 5, 9, 36, 607/37; 600/509

(56) References Cited

U.S. PATENT DOCUMENTS

| 5,228,192 A | | 7/1993 | Salatino ............... 29/827 |
|---|---|---|---|
| 5,241,960 A | * | 9/1993 | Anderson et al. ............ 607/5 |
| 5,645,586 A | * | 7/1997 | Meltzer ................. 623/31 |
| 5,776,797 A | | 7/1998 | Nicewarner, Jr. et al. ... 438/107 |
| 5,814,090 A | * | 9/1998 | Latterell et al. ............ 607/36 |
| 5,926,369 A | | 7/1999 | Ingraham et al. ........... 361/699 |
| 6,245,092 B1 | | 6/2001 | Schaldach, Jr. et al. ....... 607/1 |

OTHER PUBLICATIONS

Engmark et al, United States Patent Application Publication, US 2003/0040779–A1, Feb. 27, 2003.*

* cited by examiner

*Primary Examiner*—Carl Layno
(74) *Attorney, Agent, or Firm*—Steven M. Mitchell

(57) ABSTRACT

An implantable cardiac rhythm management device has a flexible circuit sheet with a number of connected sheet portions and a number of conductive traces extending between different sheet portions. A plurality of device components are attached to the sheet, on different sheet portions. The sheet is articulated at fold lines between the sheet portions; and folded so that at least some of the sheet portions occupy different planes.

19 Claims, 6 Drawing Sheets

IMPLANTABLE CARDIOVERTER DEFIBRILLATOR HAVING AN ARTICULATED FLEXIBLE CIRCUIT ELEMENT AND METHOD OF MANUFACTURING

FIELD OF THE INVENTION

This invention relates to electronic components for implantable medical devices, and more particularly implantable cardioverter/defibrillators having compact circuitry.

BACKGROUND OF THE INVENTION

Implantable Cardioverter Defibrillators (ICDs) are implanted in patients susceptible to cardiac tachyarrhythmias including atrial and ventricular tachycardias and atrial and ventricular fibrillation. Such devices typically provide cardioversion or defibrillation by delivering low voltage pacing pulses or high voltage shocks to the patient's heart, typically about 500–800V. The ICD operates by detecting a fast heart rate or tachyarrhythmia, upon which a battery within the device housing is coupled via an inverter to a high voltage capacitor or capacitor pair to charge the capacitors. When the capacitor reaches a desired voltage, charging is stopped and the capacitors are discharged under control of a microprocessor to provide a therapeutic shock to the patient's heart.

It is desirable for ICDs to be as small as possible, primarily for patient comfort. However, it is also important to provide adequate stored energy in the device battery to allow a useful device life before surgical replacement is required. Also, device capacitors must have adequate capacitance to store and deliver a suitable charge for therapy. Advancements have permitted reductions in the size of these components. However, even for the most advanced components, there remains a desire to minimize device size.

In addition, while batteries and capacitors have traditionally been the largest device components, and therefore the primary targets for miniaturization, advancements for these components have resulted in other components having a significant effect on device size.

A ceramic hybrid is normally used for supporting the many electronic components (including integrated circuit controllers and discrete components), for connecting to the larger components such at the battery and capacitor, and for providing electrical interconnections between components. Such ceramic hybrids require significant area to mount all required components, increasing the needed area. While multi-layer boards having more than two conductive trace layers are available, these do not provide additional mounting area. In addition, even if adequate area is provided, the additional buried traces can lead to heat build-up where current flows beneath heat-generating components.

Moreover, there are disadvantages to mounting components too densely on a board even if there were adequate area. Heat generated by components can impair the function of adjacent components, or those mounted on the opposite side of the board at the same location. In ICD circuitry, certain high voltage sections of the circuit can generate parasitic capacitance, noise and interference at levels that may impair the function of low voltage circuitry immediately adjacent to or on the opposite side of the high voltage circuitry. High voltage standoff distances must be maintained to prevent arcing or shorting from one component at one potential to another at a different potential. High voltage standoff rules tend to increase the surface area that is required for a high voltage circuit.

SUMMARY OF THE INVENTION

The disclosed embodiment overcomes the limitations of the prior art by providing an implantable cardiac rhythm management device. The device has a flexible circuit sheet with a number of connected sheet portions and a number of conductive traces extending between different sheet portions. A plurality of device components are attached to the sheet, on different sheet portions. The sheet is articulated at fold lines between the sheet portions; and folded so that at least some of the sheet portions occupy different planes.

BRIEF DESCRIPTION OF THE DRAWINGS

Further features and advantages of the present invention may be more readily understood by reference to the following description taken in conjunction with the accompanying drawings, in which.

DETAILED DESCRIPTION OF A PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
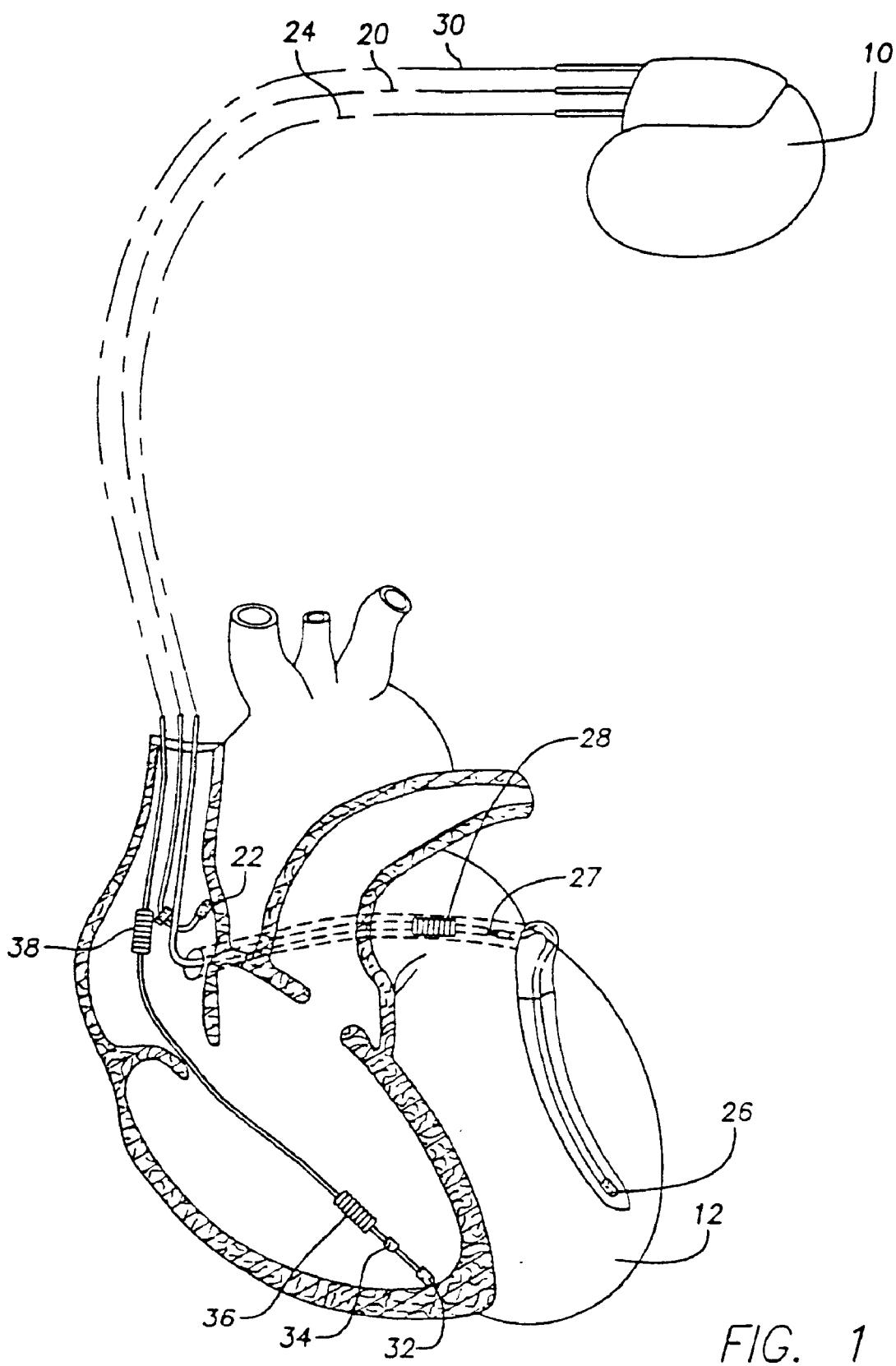
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculattire of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a Superior Vena Cava (SVC) coil electrode 38. Typically, the right ventricular lead 30 is transvenously inserted into the heart 12 so as to place the right ventricullar tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
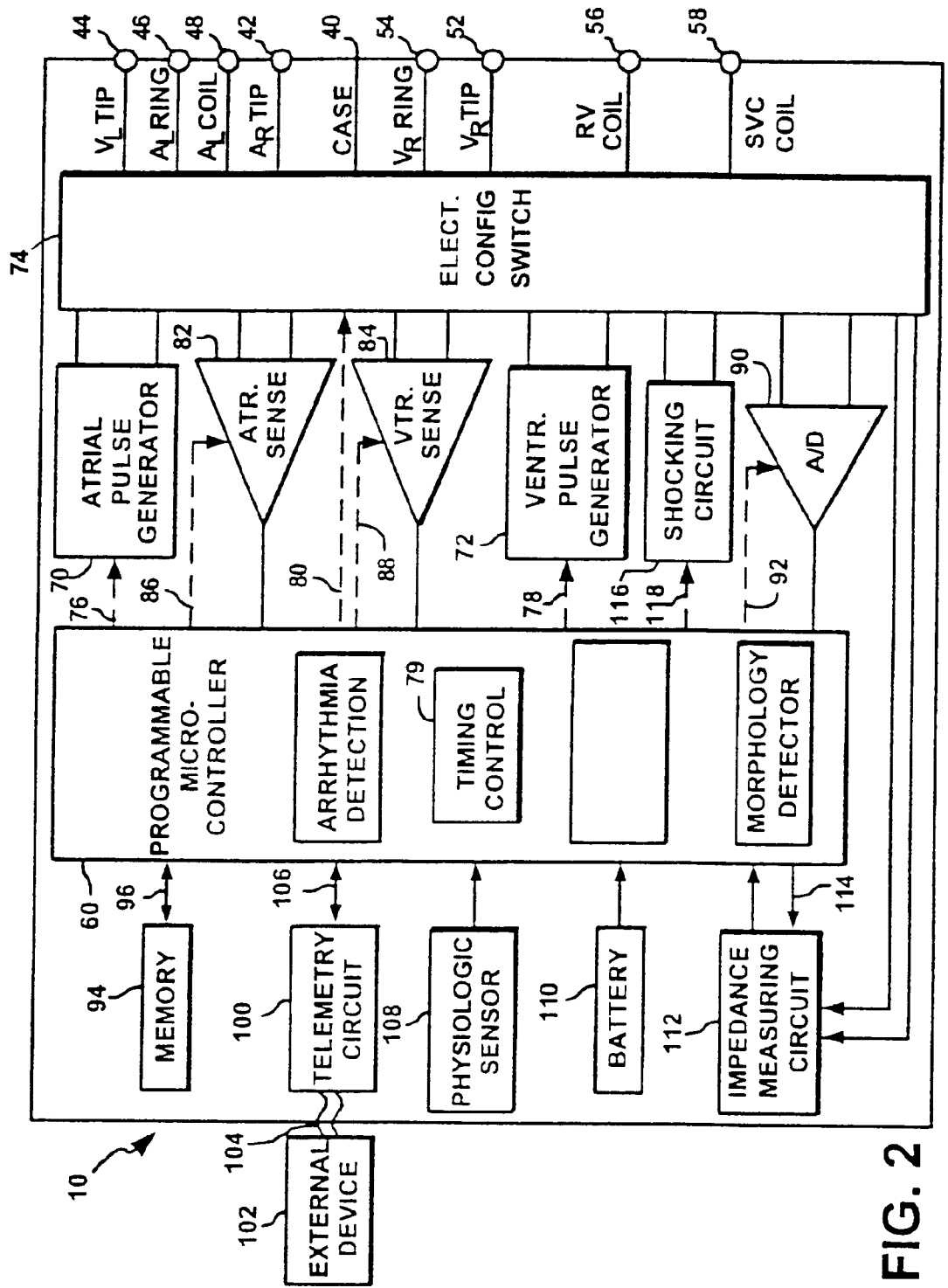
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricullar ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 µA), and then be capable of providing high-current pulses (for capacitor charging) when the patient requires a shock pulse (preferably, in excess of 2A, at voltages above 2 V, for periods of 10 seconds or more). The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114.

In the case where tile stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
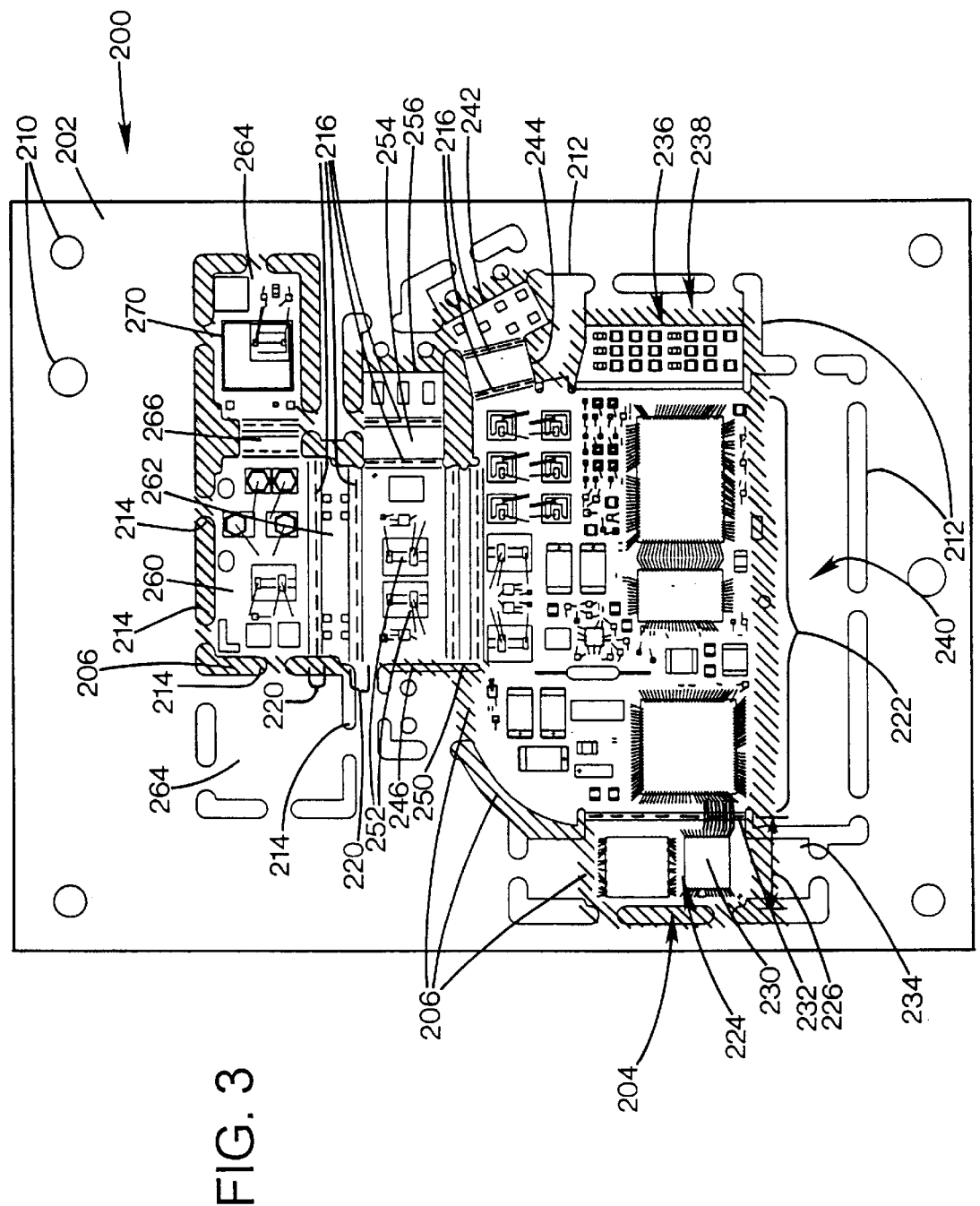
FIG. 3 is a plan view of a circuit element according to the preferred embodiment of the invention.

FIG. 3 illustrates a circuit sheet 200 employed in the disclosed device. The sheet is a rectangular polyimide film with a thickness in the range of 0.003 to 0.005 inch, a width of approximately 3 inches, and a length of approximately 4 inches. The sheet includes conductive copper foil traces on each major surface. The sheet has a frame 202 that fully encompasses a circuit element 204, the boundaries of which are indicated by a peripheral cut line 206. The sheet frame includes a number of registration holes 210 that are used to secure the sheet to a fixture in the illustrated flat configuration during manufacturing and assembly. A number of border slot segments 212 provide a pre-cut separation of selected sheet portions and the frame. Some slots are aligned with the cut line, to reduce the amount of cutting needed to free the circuit element 204 from the frame. Other slots serve to divide sacrificial sheet test portions (to be discussed below) which are initially attached to the circuit element, but which are eventually separated from the frame. The slots each have limited length, to ensure that the periphery of the circuit element is well supported by spans 214 that define the ends of the slots. Preferably, the slots are no longer than 0.75 inch long, and each span has width at its narrowest portion of at least 0.08 inch.

The circuit element has a number of different portions, which are connected together in a single integral unit, and which are generally divided from each other at straight border or fold lines 216, shown as dashed lines. As will be discussed below, the sheet portions are folded with respect to their adjacent portions at these lines. Preferably, a narrow straight strip region 220 is provided at each fold line. The strip is preferably a region of reduced sheet stiffness. In the preferred embodiment, this is provided by limiting the electrically conductive metal traces only to the width needed as they cross the strip, and using maximum plating on the sheet portions adjacent to the strip. Minimum spaces and maximum traces can provide this, or an otherwise blank region, such as on an unused back side of the sheet, may be fully plated as a ground plane.

Other alternative means to provide reduced relative stiffness include a row of perforations, a partial depth score line, or the absence of a covering layer at the strip while the adjacent portions are covered. Preferably, there is adequate stiffness differential that manual bending of the sheet at the fold line generates a sharp bend at the line, while the adjoined portions remain flat. In addition, the used of adequate ductile metallization extending across the fold line to provide connections between the different portions serves to allow the folds to be preserved, due to the permanent deformation of the metal layer.

The circuit element has a main portion 222 having a generally rectangular shape, with several different sheet portions extending from different fold line locations along the periphery of the main portion. In alternative embodiments, the main portion may have any selected shape, preferably to closely conform to the shape of the housing chamber and adjacent components. The main portion is the largest portion, and generally defines the area of the entire circuit elements after it has been folded, as will be discussed below. The main portion is approximately 2.5 inches wide and approximately 1.5 inches tall. For this discussion, directions are given in terms of the FIG. 3 orientation, although this orientation is not necessarily preserved after folding and installation, or in other Figures. The main portion includes a large number of electrically connected and mechanically supported electronic components, including application specific integrated circuits (ASIC), resistors, capacitors, and inductors such as the DC to DC converter and the telemetry coil. These components are placed on the main portion in close proximity to each other to facilitate ease of assembly and rework if required. Since the interconnect density between components is the highest in this region, locating these components on the main portion makes the circuit assembly easier and less costly to fabricate. Almost all of the components in the preferred embodiment are mounted on a single side of the circuit element where possible to facilitate ease of assembly. On the main portion, as on other portion, the components are widely and generally evenly distributed to spread out heat generated in the components. The components are preferably surface mounted, avoiding the need for through-holes in the circuit, although such alternative connection methods may be employed where this is not a concern.

A controller portion 224 extends from the left edge of the main portion, and has a width 226 sized to define the height of the folded circuit element when the controller portion is folded downward (into the page) by 90 degrees. The controller portion includes at least one application specific integrated circuit (ASIC) 230. A number of traces 232 (shown as examples) extend from the controller portion's component to the main portion for connection to other components thereon. In the preferred embodiment, there are multiple traces connecting to each portion, across each fold line. Similarly, all other portions are connected to other portions, and at least indirectly to the main portion. A flap 234 near the battery extends from a lower edge of the controller portion for the purpose of providing test points to assure the SRAM (static random access memory) is functioning properly during manufacturing assembly.

Another flap 236 on the opposite side of the battery is connected to the right edge of the main portion, opposite the controller portion 224. The flap 236 has a limited width so that it does not protrude excessively when folded 90 degrees from the main portion, in the same manner of portion 224. A second battery flap 238 is connected to the free edge of flap 236, and provides a mounting surface for several passive components such as resistors and capacitors.

The remaining portions are connected to the main portion to be folded to positions that overly the main portion, residing within the periphery of the main portion to provide a compact package.

A test flap 240 is connected to tile entire lower edge of the main portion 222, and includes numerous test pads (not shown) that are connected to other components on other portions of the circuit, so that a test probe may communicate with the circuit after components have been installed, to verify proper functioning before the circuit is installed in a device.

A magnetics component hook up portion 242 is connected via an intermediate stand-off portion 244 to the upper right edge of the main portion. The stand-off portion may be folded by 90 degrees from the main portion, to define the spacing between the main portion and the hook up portion 242, which will reside parallel to the main portion when folded.

A first high-voltage portion 246 is connected via a stand-off portion 250 to the upper edge of the main portion 222, and supports an array of high voltage switching components 252. The standoff portion 250 establishes the spacing between the portion 246 and the main portion when portion 246 is folded back over the main portion. A transition portion 254 provides a connection to an output portion 256 having several lands for connecting to the lead conductors.

A second high voltage portion 260 is connected via a standoff portion 262 to the first portion 246 at the upper edge. A sacrificial test patch 264 is connected to the left edge of the second portion 260, and incudes lands for test probe contact, and conductive traces (not shown) connecting to the second portion 260 and other portions via the spans 214. A third high voltage portion 264 connects to the right edge of portion 260 via a standoff portion 266, and carries another high voltage switch, component 270, used to dissipate the high voltage charge off of the high voltage capacitors when the device makes the decision not to deliver therapy to the patient.

In general, high voltage components are located on the periphery of the circuit assembly. Fewer control lines and a small number larger cross sectional area circuit traces are required to connect these components to the main portion of the circuit assembly. This yields a simpler circuit assembly that is easier and less costly to fabricate.

The circuit element is first produced with the traces formed and the slots and holes formed. Then, the electronic components are mounted, in the preferred embodiment by an electrically conductive adhesive. A surface mount soldering process may also be used. The circuit is then tested by the application of test probes to the test flaps, and the inputting or electrical signals and monitoring of corresponding output signals to ensure that they conform to expectations. After the circuit passes this test, the circuit element is cut out of the sheet frame by a laser cutter. In alternative embodiments, the cutting may be made by any other means, such as mechanical shearing, water jet cutting, or other means. The circuit element is then folded to the desired shape shown in FIG. 4.

Figure 4:
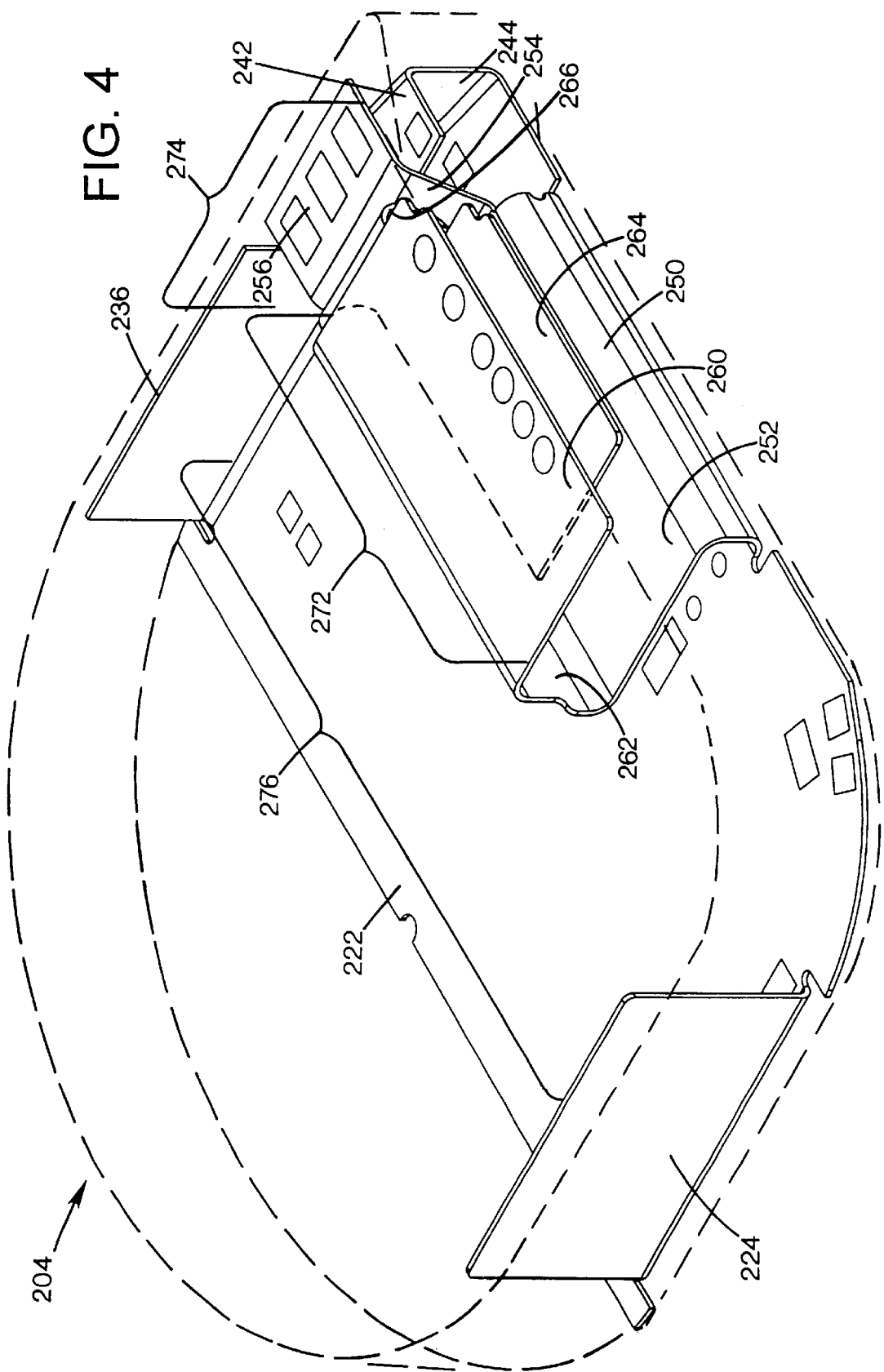
FIG. 4 is a perspective view of the circuit element of FIG. 3 in a folded configuration.

FIG. 4 shows the circuit element in simplified form, without attached components, to illustrate the folded configuration. In the illustration, the circuit element 204 is oriented so that the component side visible in FIG. 3 is facing down at the main portion. The side portions 224 and 236 are folded upward by 90 degrees so that they just reside in the space defined by the main portion periphery. Portion 242 is folded back to overlie the main portion, parallel to the main portion and offset above by a distance defined by the height of the standoff 244. Portion 252 is folded back over the main portion, and portion 254 angled upward to allow portion 256 to reside parallel to and above portion 242. Portion 264 is folded against portion 260, which is folded over portion 252 with portion 264 captured in between.

Thus, a four-layer stack 272 of circuit sheet are stacked in parallel, including portions 222, 252, 264, and 260. A three layer stack 274 is formed with portions 256, 242, and 222. Each stack has a limited height that is less than or only slightly greater than the height by which the side portions 224 and 236 protrude above the plane of the main portion. Together, the stacks are compactly positioned adjacent each other in an essentially rectangular group. A large clear rectangular region 276 of the main portion remains open between the side portions 224, 236, free of any overlapping folded portions. The clear region 276, as also shown in FIG. 5, is free of surface-mounted components, which are mounted on the opposite surface.

Figure 5:
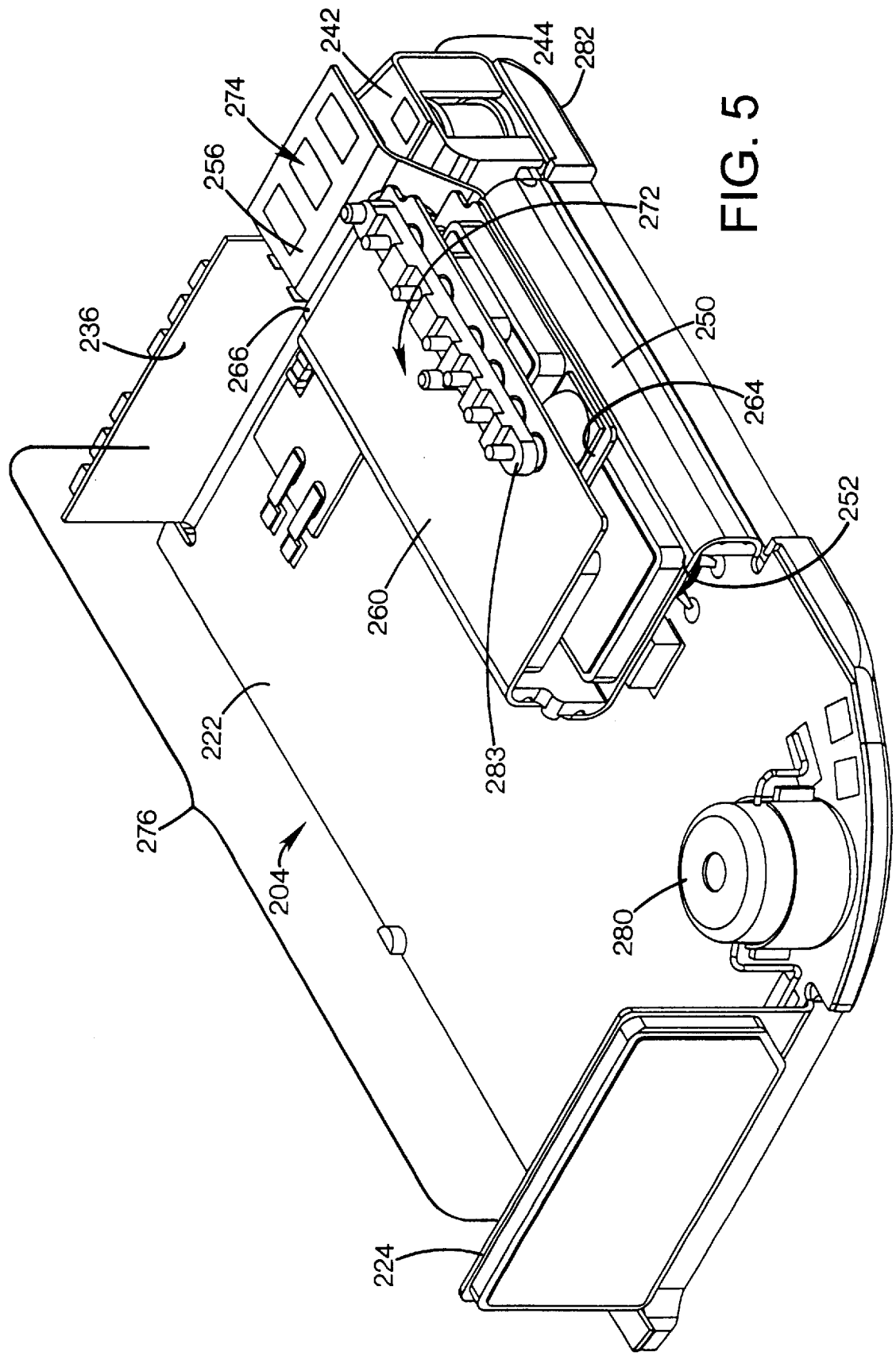
FIG. 5 is a perspective view of the circuit element of FIG. 3 in a folded configuration with attached components.

As further shown in FIG. 5, components are mounted to the portions 224 and 236 on the sides facing away from the clear region. An inductor component 280 is connected to the upper (non-component) side of the main portion beside of the stack 272, and away from the clear portion. A plastic shell 282 underlies the main portion, extending to the periphery thereof, and enclosing and protecting the components mounted to the lower side of the main portion. An auxiliary flex circuit 283 is connected on the non-component upper side of portion, at the upper surface of stack 272, and supports the components required on the input side of the high voltage charging circuit.

Figure 6:
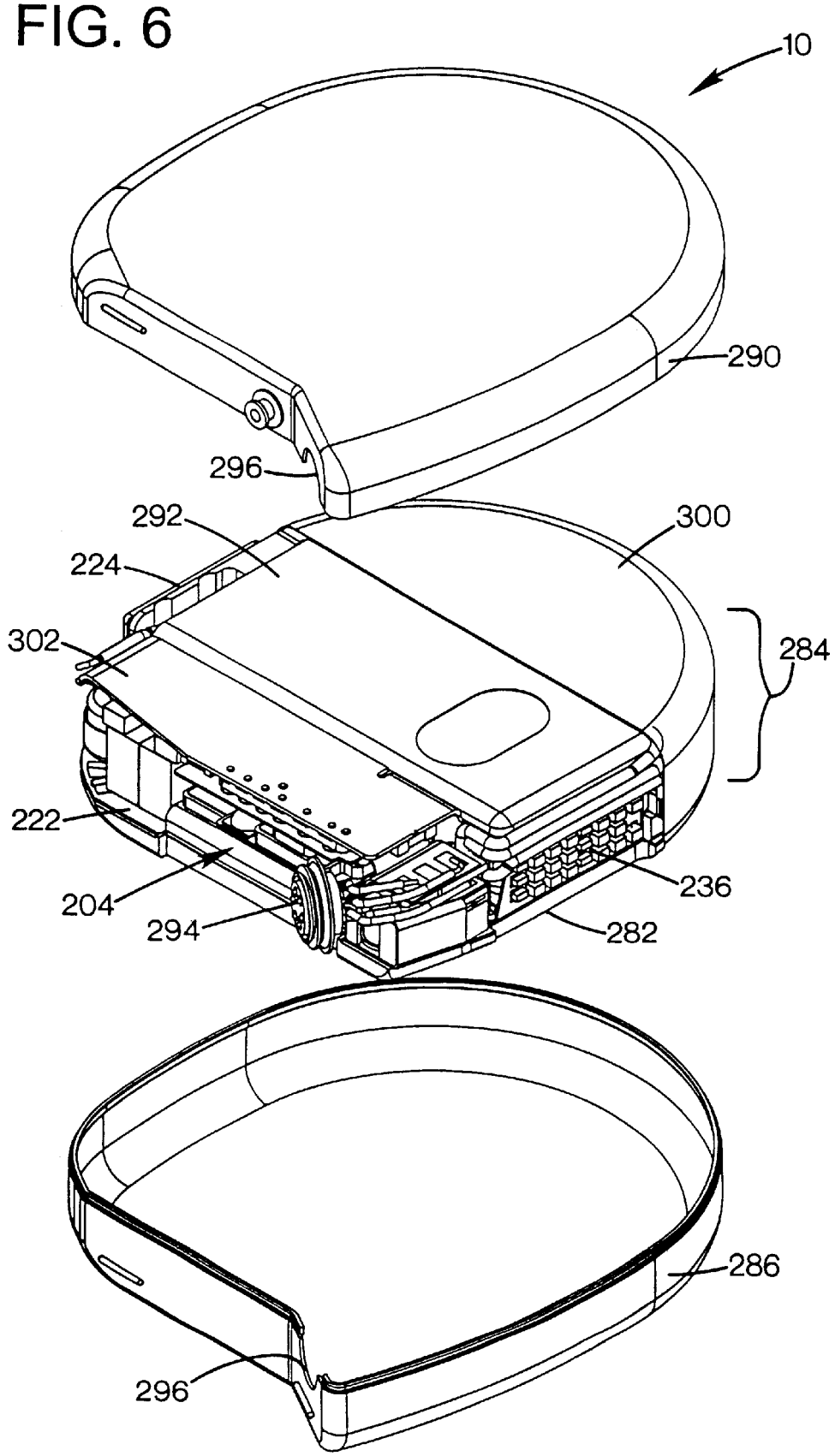
FIG. 6 is an exploded view of the device of FIG. 1.

FIG. 6 shows the entire device 10, with an assembled internal component group 284 separated from housing portions 286, 290. The housing shells 286, 290 are symmetrical (although they need not be in alternative embodiments), and are thin walled shells that minimally contribute to the device dimensions, and which define a chamber that closely receives the device components, following their profile. A rectangular battery 292 is closely received in the clear space 276, and a height comparable to the stack 272 and the upstanding portions 224 and 236. The battery extends to the upstanding portions on its ends, and abuts the stack at one major edge, and extends to the free edge of the main portion. A feed-through element 294 provides for sealed passage of conductors to the lead (not shown), and is received in semi-circular cutouts 296 in the housing portions. A semi-circular capacitor assembly 300, consisting of two capacitors connected in series, has a straight edge abutting the battery, and a curved edge defining the edge of the device away from the circuit element 204. Each capacitor has a thickness comparable to one half that of the battery plus that of the circuit main portion, and to the stacks of the circuit, so that essentially the all components have the same limited thickness. An insulating shield 302 atop the circuit element stacks protects exposed components from contact with the metal housing.

While described in terms of a preferred embodiment, the invention need not be so limited.

What is claimed is:

1. An implantable cardiac rhythm management device, comprising:

a flexible circuit sheet having a plurality of connected sheet portions, at least a first one of the sheet portions being folded to overlay a second one of the sheet portions in parallel to the first portion and spaced apart therefrom;

the sheet having a plurality of conductive traces;

at least some of the traces extending between different sheet portions;

a plurality of device components attached to the sheet;

at least some of the components attached to different sheet portions;

an electronic component connected to one of the first and second sheet portions, and positioned between the first and second portions;

the sheet being articulated at fold lines between the sheet portions; and at least some of the sheet portions occupying different planes.

2. An implantable cardiac rhythm management device, comprising:

a flexible circuit sheet having a plurality of connected sheet portions, including a main sheet portion having a plurality of different sheet portions connected to different locations along a periphery of thee main sheet portion;

the sheet having a plurality of conductive traces;

at least some of the traces extending between different sheet portions;

a plurality of device components attached to the sheet;

at least some of the components attached to different sheet portions;

the sheet being articulated at fold lines between the sheet portions; and at least some of the sheet portions occupying different planes.

3. The device of claim 2 wherein at least two of the different sheet portions are folded back to overlay the main sheet portion and to overlay each other.

4. An implantable cardiac rhythm management device, comprising:

a flexible circuit sheet having a plurality of connected sheet portions;

the sheet having a plurality of conductive traces;

at least some of the traces extending between different sheet portions;

a plurality of device components attached to the sheet;

at least some of the components attached to different sheet portions;

the sheet being articulated at fold lines between the sheet potions; and at least some of the sheet portions occupying different planes, and wherein at least a first one of the sheet portions is angled with respect to a connected second sheet portion.

5. The device of claim 4 wherein the first sheet portion is offset at a right angle from the second sheet portion.

6. An implantable cardiac rhythm management device, comprising:

a flexible circuit sheet having a plurality of connected sheet portions;

the sheet having a plurality of conductive traces;

at least some of the traces extending between different sheet portions;

a plurality of device components attached to the sheet;

at least some of the components attached to different sheet portions;

the sheet being articulated at fold lines between the sheet portions;

at least some of the sheet portions occupying different planes;

a housing defining a planar chamber containing the sheet; and wherein the sheet includes a main portion substantially extending to the periphery of at least a major portion of the chamber.

7. The device of claim 6 wherein the housing includes a peripheral side wall, and wherein at least one of the sheet portions is angled with respect to the main portion and adjacent to and parallel to a portion of the side wall.

8. An implantable cardiac rhythm management device, comprising:

a flexible circuit sheet having a plurality of connected sheet portions including a main portion having a first portion overlaid by a plurality of folded sheet portions, and having a second portion free of other sheet portions and overlaid by a battery;

the sheet having a plurality conductive traces;

at least some of the traces extending between different sheet portions;

a plurality of device components attached to the sheet;

at least some of the components attached to different sheet portions;

the sheet being articulated at fold lines between the sheet portions; and at least some of the sheet portions occupying different planes.

9. A method of manufacturing an implantable cardiac rhythm management device, comprising:

generating a circuit of conductive traces on a flexible sheet including two layers of traces, one layer on each face of the sheet;

mounting a plurality of electronic components to at least some of the sheet portions;

cutting the sheet to define a periphery of a circuit element having a plurality of sheet portions;

the sheet portions abutting each other at border lines;

folding the sheet at the border lines to displace at least some of the sheet portions into different planes;

connecting a battery and a capacitor to the circuit element; and installing the circuit element into a device housing.

10. The method of claim 9 wherein at least a plurality of the sheet portions including mounted electronic components.

11. The method of claim 10 wherein folding includes positioning a first sheet portion overlaying and parallel to a second sheet portion.

12. The method of claim 11 wherein each of the first and second sheet portions includes an electronic component.

13. A method of manufacturing an implantable cardiac rhythm management device, comprising:

generating a circuit of conductive traces on a flexible sheet;

mounting a plurality of electronic components to at least some of the sheet portions;

cutting the sheet to define a periphery of a circuit element having a plurality of sheet portions;

the sheet portions abutting each other at border lines;

folding the sheet at the border lines to displace at least some of the sheet portions into different planes;

connecting a battery and a capacitor to the circuit element;

installing the circuit element into a device housing; and electronically testing the circuit and mounted components prior to cutting the sheet.

14. The method of claim 13 wherein testing includes contacting a test portion of the sheet, and wherein cutting includes cutting away the test portion.

15. A method of manufacturing an implantable cardiac rhythm management device, comprising:

generating a circuit of conductive traces on a flexible sheet;

mounting a plurality of electronic components to at least some of the sheet portions;

cutting the sheet to define a periphery of a circuit element having a plurality of sheet portions;

the sheet portions abutting each other at border lines;

folding the sheet at the border lines to displace at least some of the sheet portions into different planes, wherein folding includes positioning a first sheet portion overlaying a limited portion of a second sheet portion, and including positioning the battery over a portion of the second portion other than the limited portion;

connecting a battery and a capacitor to the circuit element; and installing the circuit element into a device housing.

16. A method of manufacturing an implantable cardiac rhythm management device, comprising:

generating a circuit of conductive traces on a flexible sheet wherein the sheet includes a main portion having a periphery, and a plurality of attached portions at different locations about the periphery;

mounting a plurality of electronic components to at least some of the sheet portions;

cutting the sheet to define a periphery of a circuit element having a plurality of sheet portions;

the sheet portion abutting each other at border lines;

folding the sheet at the border lines to displace at least some of the sheet portions into different planes, and wherein folding includes folding the attached portions to positions within the periphery;

connecting a battery and a capacitor to the circuit element; and installing the circuit element into a device housing.

17. An implantable cardiac rhythm management device, comprising:

a flexible circuit sheet having a plurality of connected sheet portions;

the sheet having a plurality of conductive traces including two layers of traces, one layer on each face of the sheet;

at least some of the traces extending between different sheet portions;

a plurality of device components attached to the sheet;

at least some of the components attached to different sheet portions;

the sheet being articulated at fold lines between the sheet portions;

at least some of the sheet potions occupying different planes; and wherein at least a first one of the sheet portions is folded to overlay a second one of the sheet portions in parallel to the first portion and spaced apart therefrom.

18. An implantable cardiac rhythm management device, comprising:

a flexible circuit sheet having a plurality of connected sheet portions;

the sheet having a plurality of conductive traces;

at least some of the traces extending between different sheet portions;

a plurality of device components attached to the sheet;

at least some of the components attached to different sheet portions;

the sheet being articulated at fold lines between the sheet portions; at least some of the sheet portions occupying different planes; and wherein at least a first one of the sheet portions is angled with respect to a connected second sheet portion.

19. An implantable cardiac rhythm management device, comprising:

a flexible circuit sheet having a plurality of connected sheet portions;

the sheet having a plurality of conductive traces;

at least some of the traces extending between different sheet portions;

a plurality of device components attached to the sheet;

at least some of the components attached to different sheet portions;

the sheet being articulated at fold lines between the sheet portions;

at least some of the sheet portions occupying different planes; and wherein the sheet has a main portion having a first portion overlaid by a plurality of folded sheet portions, and having a second portion free of other sheet portions and overlaid by a battery.

* * * * *